(12) United States Patent
Withrow, III et al.

(10) Patent No.: US 9,588,114 B2
(45) Date of Patent: Mar. 7, 2017

(54) FLOW THROUGH TESTING SYSTEM WITH PRESSURE INDICATOR

(71) Applicant: MONTECITO BIO SCIENCES LTD, Santa Monica, CA (US)

(72) Inventors: Edward W. Withrow, III, Malibu, CA (US); Jorn Gorlach, Manchester, NJ (US)

(73) Assignee: MONTECITO BIO SCIENCES LTD, Santa Monica, CA (US)

( * ) Notice: Subject to any disclaimer, the term of this patent is extended or adjusted under 35 U.S.C. 154(b) by 0 days.

(21) Appl. No.: 14/786,272

(22) PCT Filed: Apr. 23, 2014

(86) PCT No.: PCT/US2014/035073
§ 371 (c)(1),
(2) Date: Oct. 22, 2015

(87) PCT Pub. No.: WO2014/176306
PCT Pub. Date: Oct. 30, 2014

(65) Prior Publication Data
US 2016/0084831 A1    Mar. 24, 2016

Related U.S. Application Data

(60) Provisional application No. 61/814,916, filed on Apr. 23, 2013.

(51) Int. Cl.
*G01N 21/75* (2006.01)
*G01N 31/22* (2006.01)
*G01N 33/543* (2006.01)
*B01L 3/00* (2006.01)
*G01N 33/52* (2006.01)

(52) U.S. Cl.
CPC ........ *G01N 33/54386* (2013.01); *B01L 3/502* (2013.01); *G01N 33/54366* (2013.01); *B01L 2300/047* (2013.01); *B01L 2300/069* (2013.01); *B01L 2300/0681* (2013.01); *B01L 2400/049* (2013.01); *B01L 2400/0478* (2013.01)

(58) Field of Classification Search
None
See application file for complete search history.

(56) References Cited

U.S. PATENT DOCUMENTS 2,800,458 A    7/1957    Green .......................... 252/316
3,015,128 A    1/1962    Somerville .................... 18/2.6
(Continued)

OTHER PUBLICATIONS

International Preliminary Report on Patentability in PCT/US14/35073, Nov. 15, 2015, PCT.
(Continued)

*Primary Examiner* — Jill Warden
*Assistant Examiner* — Brittany Fisher
(74) *Attorney, Agent, or Firm* — Licata & Tyrrell P.C.

(57) ABSTRACT

A device for performing immunoassays on analytes is provided. The device includes an immunosorbent membrane, an absorbent material, a piston component located below said absorbent material to draw analytes in a sample through the immunosorbent membrane into the absorbent material, and discrete groups of pressure-sensitive microcapsules located on the immunosorbent membrane.

2 Claims, 2 Drawing Sheets

(56) References Cited

U.S. PATENT DOCUMENTS

| | | | |
|---|---|---|---|
| 3,016,308 A | | 1/1962 | Macaulay .................... 117/36.7 |
| 3,173,878 A | | 3/1965 | Reyes .......................... 252/316 |
| 3,469,439 A | * | 9/1969 | Roberts .................. B01J 13/02 |
| | | | 428/402.2 |
| 3,870,639 A | | 3/1975 | Moore et al. ................. 210/359 |
| 3,888,629 A | | 6/1975 | Bagshawe .................. 23/230 B |
| 4,057,499 A | | 11/1977 | Buono ......................... 210/136 |
| 4,090,850 A | | 5/1978 | Chen et al. ..................... 23/259 |
| 4,189,385 A | | 2/1980 | Greenspan .................... 210/136 |
| 4,366,241 A | | 12/1982 | Tom et al. ......................... 435/7 |
| 4,424,279 A | | 1/1984 | Bohn et al. .................... 436/534 |
| 4,632,901 A | | 12/1986 | Valkirs et al. ..................... 435/5 |
| 4,727,019 A | | 2/1988 | Valkirs et al. ..................... 435/5 |
| 4,797,260 A | * | 1/1989 | Parker .................... B01D 61/18 |
| | | | 210/416.1 |
| 4,871,683 A | * | 10/1989 | Harris .................... B01L 3/502 |
| | | | 422/64 |
| 5,137,691 A | * | 8/1992 | Parker ............. G01N 33/54366 |
| | | | 422/69 |
| 5,811,366 A | | 9/1998 | Chikami ...................... 503/201 |
| 6,287,783 B1 | | 9/2001 | Maynard et al. .............. 435/7.1 |
| 7,205,159 B2 | | 4/2007 | Cole et al. .................... 436/518 |
| 8,012,770 B2 | * | 9/2011 | Siciliano .............. B01L 3/5023 |
| | | | 422/401 |
| 8,067,246 B2 | | 11/2011 | Marlborough et al. ...... 436/518 |
| 8,183,059 B2 | | 5/2012 | Siciliano et al. ............. 436/518 |
| 2006/0160205 A1 | | 7/2006 | Blackburn et al. ........ 435/287.2 |
| 2011/0290669 A1 | | 12/2011 | Davis et al. ............... 205/777.5 |

OTHER PUBLICATIONS

International Search Report and Written Opinon in PCT/US14/35073, Sep. 15, 2014, PCT.

* cited by examiner

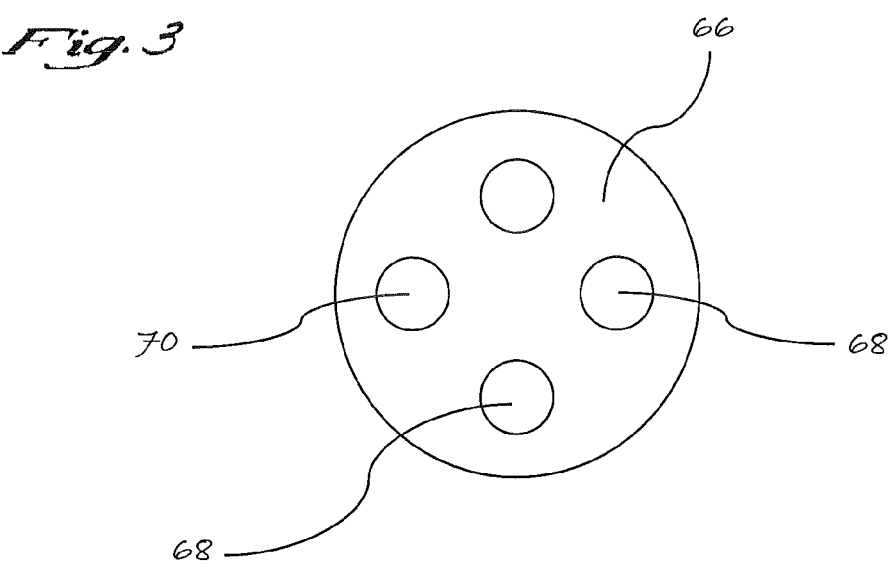

FLOW THROUGH TESTING SYSTEM WITH PRESSURE INDICATOR

This application is a U.S. National Stage Application of PCT/US2014/035073 filed Apr. 23, 2014 and claims the benefit of priority to U.S. Provisional Application Ser. No. 61/814,916 filed Apr. 23, 2013, the contents of each of which are incorporated herein by reference in their entirety.

BACKGROUND

Techniques for performing an immunoassay are generally well known in the art. For example, conventional enzyme immunoassay procedures involve a series of steps wherein an analyte in a sample material is initially bound to a corresponding antigen or antibody reagent. A second antigen or antibody is then introduced into the sample which has been labeled or conjugated with an enzyme or other substance capable of detection when treated with an additional suitable indicator reagent such as a chromogen or dye to produce a signal which is then read to indicate the absence or presence of the antigen or antibody in the sample.

Solid-phase immunoassay procedures are preferred over other diagnostic methods because of their safety, ease of use, specificity and sensitivity. Examples of such solid-phase assays include those described in U.S. Pat. No. 3,870,639; U.S. Pat. No. 3,888,629; U.S. Pat. No. 4,057,499; U.S. Pat. No. 4,090,850; U.S. Pat. No. 4,189,385; U.S. Pat. No. 4,366,241; U.S. Pat. No. 4,424,279; U.S. Pat. No. 4,632,901; U.S. Pat. No. 4,727,019; U.S. Pat. No. 4,797,260; U.S. Pat. No. 5,137,691; U.S. Pat. No. 6,287,783; U.S. Pat. No. 7,205,159; U.S. Pat. No. 8,012,770; U.S. Pat. No. 8,067,246; and U.S. Pat. No. 8,183,059.

SUMMARY OF THE INVENTION

This invention is a device for performing immunoassays on analytes. The device includes an immunosorbent membrane with an upper and lower surface; an absorbent material positioned adjacent to and below the lower surface of the immunosorbent membrane; a piston component located below said absorbent material, wherein said piston component reduces air pressure of the device and draws analytes in a sample through the immunosorbent membrane into the absorbent material; and discrete groups of pressure-sensitive microcapsules located on the upper surface of the immunosorbent membrane, wherein each group of microcapsules has a different predetermined average burst strength. In one embodiment, each group of microcapsules includes a dye that is different from the dye of any other of said groups.

BRIEF DESCRIPTION OF THE DRAWINGS

FIG. 3 is a top view of the immunosorbent membrane of the invention.

DETAILED DESCRIPTION OF THE INVENTION

Figure 1:
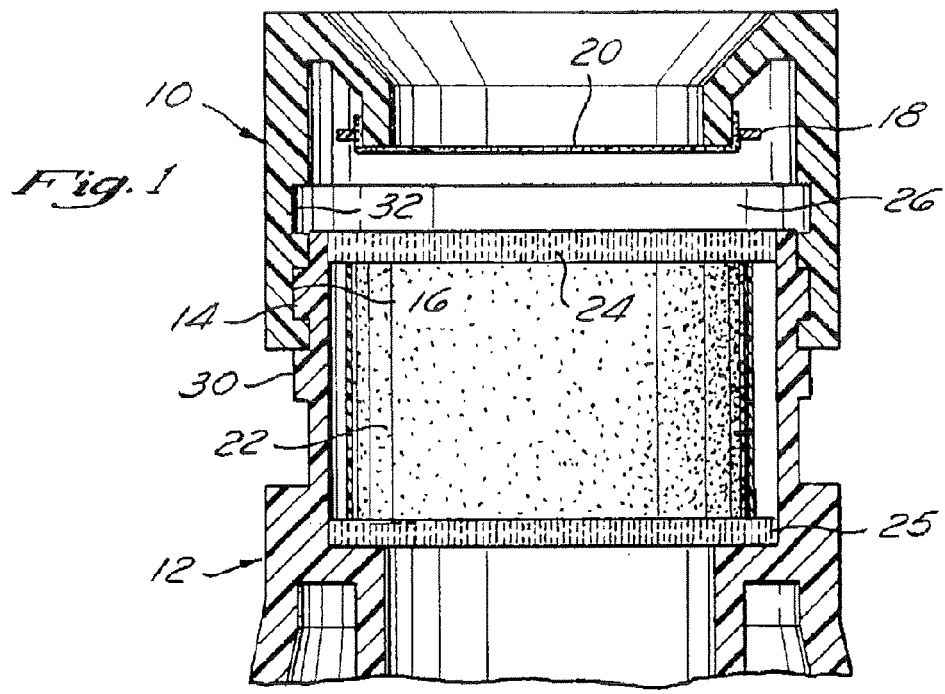
FIG. 1 is a cut away side view of a device of the invention.

The present invention provides an assay device having an externally manipulable piston for creating a region of reduced air pressure beneath a membrane containing an analytic compound, preferably a receptor or antibody. The region of reduced pressure causes a fluid sample to be tested to be rapidly drawn through the membrane. To ensure that a sufficient reduction in pressure is achieved so that all of the sample contacts the analytic compound, the membrane further includes a pressure sensing means.

In particular embodiments of this invention, an immunoassay device is provided for determining the presence and/or amount of an analyte in a sample. In accordance with this embodiment, the device has an immunosorbent membrane with one or more binding agents non-diffusively bound to its upper surface. As used herein, an "immunosorbent membrane" refers to a porous support membrane having at least one antibody (polyclonal or monoclonal antibody), antibody fragment or derivative thereof, aptamer, or other non-protein based entity (e.g., a carbohydrate or lipid), which specifically binds to a cognate epitope. In particular, the porous material is a thin disk of material such as nitrocellulose, nylon (e.g., cast from nylon 6,6 polymer) or polyvinylidene difluoride (PDVF).

As used herein, a sample or analyte solution refers to any sample suspected of containing a particular analyte. While the sample may contain detectable amounts of a particular analyte, it is realized that a sample may contain no analyte, or, in other words, the test for that ligand is negative. The sample can be of biological or environmental origin. Examples of biological samples include whole blood, serum, plasma, amniocentesis fluid, pleural fluid, peritoneal fluid, sputum, urine, feces, cerebrospinal fluid, exudates, extracts of skin or tissue specimens, swabs from the throat or wounds and the like. Examples of environmental samples include water specimens (e.g., drinking water or streams), extracts of soil samples, swabs of shipping packages, food samples, and the like. In this respect, an "analyte" refers to any material that can be involved in an antibody:antigen reaction. Typically the analyte will be an antigen, for example, a protein, a carbohydrate, cell walls (e.g., bacterial or fungal cell walls), virus particles and small molecule haptens. Other examples include molecules such as cocaine, morphine, progesterone, luteinizing hormone-releasing hormone, or DNA. It is also possible that the analyte is an antibody that reacts with a bound antigen or an antibody to the antibody.

The device of this invention is composed of an immunosorbent membrane with an upper and lower surface; a means for absorbing liquid positioned adjacent to and below the lower surface of the immunosorbent membrane; a piston component located below said means for absorbing liquid, wherein said piston component reduces air pressure of the device and draws analytes in a sample through the immunosorbent membrane into the means for absorbing liquid; and discrete groups of pressure-sensitive microcapsules located on the upper surface of the immunosorbent membrane, wherein each group of microcapsules has a different predetermined average burst strength.

More particularly, the device of the invention is composed of an immunosorbent membrane with an upper and lower surface; an absorbent material adjacent to and below the lower surface of the immunosorbent membrane, said immunosorbent membrane and said absorbent material being spaced apart in a first position with said immunosorbent membrane, spaced above said absorbent material, thereby creating an air gap therebetween, said absorbent material and said immunosorbent membrane being movable to a second position wherein said immunosorbent membrane substantially contacts said absorbent material, thereby allowing liquid to be drawn through said immunosorbent member and into said absorbent material; a piston component located below said absorbent material, said piston component being movable from a first position to a second position in order to reduce air pressure in said air gap, and thereby aiding in drawing analytes through said membrane, past said air gap, and into said absorbent material; and discrete groups of pressure-sensitive microsorbent membrane, wherein each group of microcapsules has a different predetermined average burst strength.

Referring to FIG. 1, the device of the invention has a cap member 10 mated to a body member 12 by engaging a first snap ring 14 with a first snap ring receiver 16. A retaining ring 18 is friction fit within the cap, thereby securely retaining the immunosorbent membrane 20.

A mass of absorbent material 22 is disposed within the body cavity. As used herein, "absorbent material" refers to any material that absorbs liquid. The material can be a filter material, a monolithic solid such as cellulose or cellulose acetate, or POREX, or it can be a granular solid desiccant. Examples of suitable desiccants include silica gel, calcium chloride, and the like. The preferred desiccant is a mixture of a granular powdered desiccant such as DRIERITE (anhydrous calcium sulfate) and a granular powdered absorbent such as CELITE (diatomaceous earth). It is preferred that the absorbent material be able to absorb as much liquid as possible. In some embodiments, a first retaining screen 24 holds the absorbent material in place until use. There is an air gap 26 between the first retaining screen and the immunosorbent membrane. A second retaining screen 25 can be further provided to support the absorbent material 22.

In use, the cap member 10 is pushed downwardly, snapping into a down position, thereby contacting the membrane with the first retaining screen 24. The body has a second snap ring 30 that mates with the first snap ring receiver 32 in the down position. The first snap ring mates with a second snap ring 14 receiver 32 on the cap. In another embodiment, a funnel-filter can be attached to the sample well in the cap, and be removed when the cap is depressed.

Figure 2:
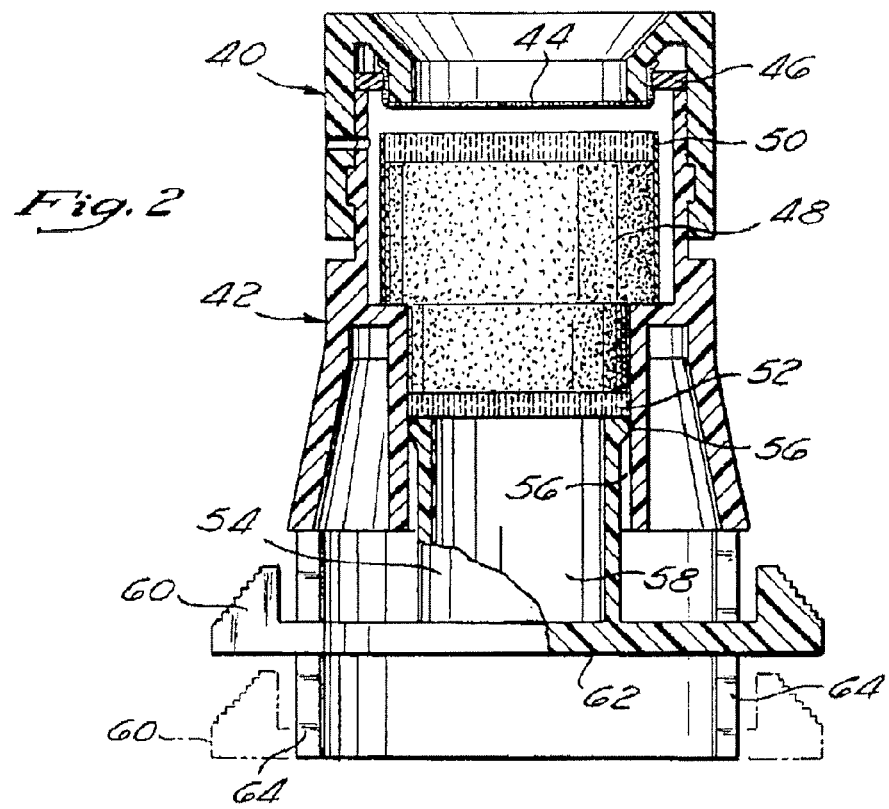
FIG. 2 is a cut away side view of a device of the invention.

Referring to FIG. 2, a cap 40 has been snap fit to a body member 42. An immunosorbent membrane 44 is secured by a retaining ring 46 and substantially all of the upper surface of the immunosorbent membrane 44 is exposed.

A mass of absorbent material 48 is disposed within the body cavity. A retaining screen 50 keeps the absorbent material in place within the body cavity, and can be made of any material that is porous enough to communicate a vacuum from the piston to the absorbent material. An optional lower retaining screen 52 is shown supporting the absorbent material. Without the lower retaining screen, the powder will settle into a relief housing of piston 54. The piston is disposed within the body at less than the uppermost possible position. In use and after the sample has incubated for the appropriate amount of time, the piston is moved to its uppermost position, thereby contacting a first retaining screen 50 with the immunosorbent membrane. The piston can then be drawn downwardly, thereby drawing liquid with it.

Absorbent material is supported on the second retaining screen. The second retaining screen is porous enough to allow the vacuum to draw liquid, but not porous enough to allow the particulate absorbent material to flow through. The second retaining screen is disposed above a piston housing 56 and is in vacuum communication with the piston housing. That is, if the piston is depressed, a zone of reduced air pressure is created that acts directly on the bottom surface of the second retaining screen. Within the piston housing, the piston member 54 is sealingly engaged with the walls of the piston housing by a gasket means 56. Preferably, the top of the circumferential wall terminates in a peripheral lip extending outwardly, which engages the walls of the piston housing as the gasket means. In a preferred embodiment, the piston has a piston wall forming a central well 58. The central well can accumulate liquid reagents or washing fluids used during the test for the analyte. Piston handles 60 attached to the piston base plate 62 extend through a slot 64 allowing external manipulation of the piston by the user. The piston handles are oppositely disposed on the piston base plate. Advantageously, the device of this invention does not require an external source of vacuum.

In an alternative embodiment, a first and second snap ring receiver are modeled into the cup, but only one snap ring is molded onto the body. The cup ring engages the first snap ring receiver in the upper position and the second snap ring receiver in the lower position.

Upon actuation of the piston component, a region of reduced pressure is created in the air gap located between the immunosorbent membrane and absorbent material. To ensure that a sufficient reduction in pressure is achieved so that all of the sample contacts the immunosorbent membrane, the immunosorbent membrane further includes a pressure sensing means. As illustrated in FIG. 3, the upper surface of immunosorbent membrane 66 includes one or more binding agents 68 bound thereto and pressure sensing means 70.

In particular embodiments, the pressure sensing means includes discrete groups of pressure-sensitive microcapsules located on the upper surface of the immunosorbent membrane, wherein each group of microcapsules has a different predetermined average burst strength. In accordance with this embodiments, the microcapsules in any one group break at substantially the same pressure. However, the pressure-sensitivity of the microcapsules in any one group differs from the pressure-sensitivity of the microcapsules in any other group. When broken, the microcapsules provide a color, color change, or color density change which is pressure-related so that a record of pressure changes and variations is produced. The microcapsules may be applied directly to the upper surface of the immunosorbent membrane or the microcapsules may be mixed with, for example, an adhesive, and thereafter applied to a surface.

When a force is applied to a surface coated with the pressure-sensitive microcapsules, in this case suction pressure created by the piston component, the most pressure-sensitive microcapsules break first and, as the pressure increases on the surface of the immunosorbent membrane, the less pressure-sensitive microcapsules break, in sequence, in proportion to their pressure-sensitivity. The pressure at which a particular microcapsule breaks is dependent upon a number of variables such as capsule size, wall and internal phase material, and wall thickness. Since each of these variables is controllable, microcapsules can be tailored to break at any desired pressure. Thus, by strict control of these variables, microcapsules can be made which differ greatly, in burst strength, for example, by 100 psi, or which differ only slightly in burst strength, for example, by 0.1 psi. In general, the more sensitive the pressure test, the less are the burst strength differences among the groups of microcapsules employed.

The microcapsules which are employed in this invention, are discrete microcapsules. As used herein, the term "discrete microcapsules" refers to microcapsules which have a single internal phase droplet or pellet surrounded by a wall.

The size of the microcapsules used herein may vary greatly and typically have a size which permits them to be readily dispersed in a binder or vehicle which can then be attached or spread on a surface. In general, the size of the microcapsules may range from about 0.1 micron to a few millimeters. As indicated, burst strength is a function, among other things, of size of microcapsule. Although substantially all of the microcapsules in a particular discrete group of microcapsules will have substantially the same size, the microcapsulation in a discrete group may differ in size from the microcapsules in another discrete group. That is, capsule size may be the variable employed to provide different burst strengths.

It will be understood that it is impossible, for practical purposes, to form a group of microcapsules in which all of the microcapsules in the group are identical, that is, which have identical burst strengths. Therefore, there will always be some variation in burst strength among the microcapsules within any one group.

It is also within the scope of this invention to employ microcapsules in which the burst strength range of each of the microcapsule groups overlaps the burst strength range of other groups. That is, when the immunosorbent membrane is subjected to certain pressures, some microcapsules in each of two pressure-sensitive adjacent groups will break. The result is that, instead of obtaining sharply defined color differences, a blended color which is a combination of the colors in each of the two microcapsule groups will be obtained. Thus, continuous pressure changes, as compared with incremental pressure changes, may be recorded by a color spectrum produced as a result of the overlapping burst strength ranges.

The microcapsules may be made by a number of known methods. It is only necessary that the method selected be capable of producing batches of microcapsules in which substantially all of the microcapsules in a batch have substantially the same burst strength. That is, the selected method should be capable of producing a batch of microcapsules in which the burst strength of substantially all of the microcapsules varies within about 5% of the average burst strength of the microcapsules in that batch. Microencapsulation processes which may be employed to produce the microcapsules of this invention include both chemical and mechanical processes. Chemical microencapsulation processes include phase separation from both aqueous and organic solvent solutions, solvent exchange in preformed capsules, interfacial polymerization and melt techniques. See, e.g., U.S. Pat. Nos. 3,016,308; 2,800,458; U.S. Pat. No. 3,173,878; and U.S. Pat. No. 5,811,366. Mechanical methods include vacuum metallizing, fluidized bed coating and centrifugal casting. See, e.g., U.S. Pat. No. 3,015,128.

The external phase or wall of the microcapsules may be made from a variety of polymeric materials including both organic and inorganic materials. The wall must be made from a material which will not melt, vaporize or otherwise fracture, except by externally-applied pressure. Examples of materials which may be used to form the walls of the microcapsules are: acrylate and methacrylate resins, such as polymethylmethacrylate and polyacrylic acid; resins produced from esters of ethylene glycol and terephthalic acid; animal glues; silica resins; polyurea resins and casein.

The wall materials may also be modified to provide the desired degree of hardness. For example, the following plasticizers may be used: adipic acid esters, such as dioctyl adipate and dibutyl adipate; biphenyl derivatives, such as chlorinated biphenyl; glycol derivatives, such as polyethylene glycol of molecular weight of 200 to 20,000, polypropylene glycols, ethylene glycol dibutyrate and ethyl phthalyl ethyl glycolate; hydrocarbons, such as butyl or isooctyl esters and glycol ethers of lauric, oleic, citric, adipic, azelaic, benzoic, palmitic, phosphoric acids, and phthalic acid derivatives, such as dimethyl-, diethyl-, dibutyl-phthalates.

To provide the colors produced upon bursting of the microcapsules, the microcapsules are provided with an internal phase which is colored or which is color producing. The color-producing, internal phase materials are materials which may themselves not be colored, but which produce colors upon, for example, contact with air when the capsule is burst or reaction with another material in the microcapsule which is shielded from the internal phase before the microcapsule is broken, but which contacts the internal phase when the microcapsule is broken.

In general, the internal phase includes two components, the colored or color-forming component and a fluid capable of suspending or dissolving the colored or color-forming component. However, it will be understood that the internal phase may be a single component which is colored or color-forming. Preferably, the internal phase has a low volatility to provide the microcapsules with a relatively long shelf life, i.e., to reduce loss of internal phase through the microcapsule walls. Additionally, the internal phase preferably has a high boiling point to reduce volatility at elevated use temperatures and to prevent fracturing of the microcapsules at elevated temperatures due to internal pressure.

In the use of this device, the sample is placed in contact with the immunosorbent membrane. After an optimum, predetermined incubation period has passed, the handles are moved upwardly which allows the first retaining screen to contact the immunosorbent membrane, thereby drawing the liquid downwardly. Should the pressure inside the air gap located between the immunosorbent membrane and absorbent material not be sufficient to draw all the sample through the immunosorbent membrane, additional suction can be provided by moving the handles downward to create a region of reduced air pressure (e.g., −0.5 to −10 psi suction pressure) which effectively draws liquids through the immunosorbent membrane. The liquid will then be in the gap on the absorbent material retainer. The liquid will flow through the retaining screen and into the absorbent powder.

It is preferred that the body member, the cap, the piston, and the retaining screens all be made of moldable plastic. Such construction provides low cost components that are easily assembled. The gasket member of the piston wall has superior wall engagement properties when made of molded plastic.

The sample concentrator funnel allows the sample solution to pass only through the receptor site on the membrane, i.e., the area of the membrane containing the binding agent. The analyte in the sample has a greater chance of reacting with the binding agent if all the sample solution passes through the receptor site, thereby significantly enhancing the sensitivity of the test.

The sample concentrator funnel can sit snugly within the funnel of the top of the cap member. The fit between the concentrator funnel and the cap can be enhanced with engagement members formed when the plastic cap is formed. It is preferable, but not mandatory, that a filter member cover the bottom of the sample concentrator funnel. Then more contaminated samples, such as essentially untreated biological samples, can be assayed with the device. Examples of such fluids include blood serum, urine, and the like.

The sample essentially contacts all of the receptor site which covers the exit from the concentrator funnel. After the sample has contacted the area of the membrane containing the binding agent, the sample concentrator funnel is removed and a test verification sample contacts the entire surface of the membrane. The test verification does not need the increased sensitivity provided by the sample concentrator funnel.

During manufacture, the desiccant is packed into the body member having the vacuum plunger in the up position. The desiccant will absorb water from the reagents placed on the membrane. When needed the plunger is moved downwardly, urging the reagents through the membrane. Although the desiccant is shown extending to the bottom of the piston member, it need not extend that far. A retaining screen can be provided that supports the absorbent material. One advantage to the use of desiccant as an absorbent material is that no extra packets of desiccant need to be added to the shipping package. Such packages of desiccant are needed when conventional absorbents such as cellulose nitrate are used. A further advantage is that desiccant can absorb as much as five times the amount of liquid that a conventional absorbent can. Therefore, larger samples can be used thereby greatly increasing the sensitivity of the test.

In use, the unit is mounted on a mounting means. The immunosorbent membrane will have been impregnated with a binding agent to an analyte that is to be tested for. For example, in a pregnancy test, the immunosorbent membrane will have been impregnated with anti-HCG. The sample solution can be either a urine sample or a blood serum sample. After the fluid has been contacted with the immunosorbent membrane and drawn into the absorbent material, a second labeled antibody is contacted with the membrane. If the analyte is present, it will be bound to the first binding agent on the upper surface of the membrane. The bound analyte then acts as a receptor and binds a second, labeled binding agent. This is sometimes referred to in the art as a "forward sandwich" assay. See, e.g., U.S. Pat. No. 4,376,110. If the analyte is present, then the label will be present on the upper surface of the membrane. The label can be a radiometric label, a fluorometric label, an enzymatic label, a colorometric label, or any of a number of other labels well known in the art. It will be appreciated that the present invention is not limited to sandwich assays, but is general for other heterogeneous assays known in the art.

One advantage of the device of the present invention is that tests can be run on a wide variety of compounds in fluids. For example, if the pH of water is to be tested in the device of the present invention, the membrane could be litmus paper. Other similar non-antibody tests will immediately suggest themselves to the skilled artisan. Of course, the preferred tests are antibody tests. The device of the present invention can facilitate tests for a wide range of antigens. A great advantage of the device is that different fluids can be tested for. For example, blood serum and urine can both be tested in the same unit.

Of course, almost any antigen can be analyzed for using the apparatus of the present invention. For example, one can test for HGC, for viral infections such as AIDS or herpes, drugs of abuse such as cocaine or heroin, difficult to diagnose bacterial diseases such as chlamydia or asymptomatic gonorrhea, and other antigens.

In a particular embodiment, at least two different binding agents are present on the immunosorbent membrane, for example, anti-HCG and anti-horseradish peroxidase. The first antibody tests for the presence of the antigen. The second can test if the reagents are working properly, that is, it should always be a positive test if the reagents are added in the correct order. When colorometric labels are used, the two antibodies can be placed on the membrane to form a pattern. For example, a minus if the test is negative, or a plus if the test is positive, or a ring and an inner dot forming a bulls eye pattern if the test is positive, and a ring if the test is negative. The membrane of this invention can be impregnated using any suitable apparatus. See, e.g., U.S. Pat. No. 4,748,042.

Advantageously, the immunoassay of this invention can be carried out by any user, including a laboratory technician or a patient. In this respect, the instant device can be used by anyone in the case of home test kits. In addition, it is possible that the device disclosed herein could be used as part of an automated testing system then the "user" of the immunoassay device would be the automated system.

What is claimed is:

1. A device for performing immunoassays on analytes comprising:
    an immunosorbent membrane with an upper and lower surface;
    an absorbent material positioned adjacent to and below the lower surface of the immunosorbent membrane;
    a piston component located below said absorbent material, wherein said piston component reduces air pressure of the device and draws analytes in a sample through the immunosorbent membrane into the absorbent material; and
    discrete groups of pressure-sensitive microcapsules located on the upper surface of the immunosorbent membrane, wherein each group of microcapsules has a different predetermined average burst strength.

2. The device of claim 1, wherein each group of microcapsules comprises a dye that is different from the dye of any other of said groups.

* * * * *